United States Patent [19]

Kubicek

[11] 4,145,352

[45] Mar. 20, 1979

[54] PREPARATION OF THIOAMIDES FROM AMIDES

[75] Inventor: Donald H. Kubicek, Bartlesville, Okla.

[73] Assignee: Phillips Petroleum Company, Bartlesville, Okla.

[21] Appl. No.: 838,343

[22] Filed: Sep. 30, 1977

[51] Int. Cl.$^2$ .............. C07C 153/057; C07C 153/063; C07D 205/06; C07D 207/24

[52] U.S. Cl. .......................... 260/326.82; 260/239 A; 260/239.3 A; 546/216; 546/243; 260/551 S

[58] Field of Search ........... 260/551 S, 326.82, 239 A, 260/239.3 A, 293.65, 293.85

[56] References Cited

U.S. PATENT DOCUMENTS

| | | | |
|---|---|---|---|
| 2,539,325 | 1/1951 | Prochazka | 260/239.3 A |
| 3,192,210 | 6/1965 | Lunsford et al. | 260/326.82 |
| 3,306,910 | 2/1967 | Louthan | 260/326.83 |
| 3,306,911 | 2/1967 | Doss | 260/326.83 |
| 3,338,913 | 8/1967 | Yates | 260/551 S |
| 4,000,159 | 12/1976 | Scoggins et al. | 260/326.82 |

OTHER PUBLICATIONS

Eilingsfeld et al., Chem. Abstracts, vol. 59, col. 15215–15216.

*Primary Examiner*—Alton D. Rollins

[57] ABSTRACT

A method for preparing thioamides from amides by contacting an amide with a source of sulfur in the presence of a sulfactive catalyst. In a preferred embodiment the sulfactive catalysts are molybdenum or tungsten and the reactants are contacted at an elevated temperature below 800° F. (427° C.).

10 Claims, No Drawings

PREPARATION OF THIOAMIDES FROM AMIDES

BACKGROUND OF THE INVENTION

This invention relates to sulfur containing compounds and the synthesis of these compounds. In one of these aspects this invention relates to the preparation of thioamides from amides. In another of its aspects this invention relates to the preparation of thiolactams from lactams. In yet another aspect this invention relates to catalyzed reactions at relatively mild reaction temperatures.

Sodium hydrosulfide is used as a source of sulfur for the preparation of a poly(arylene sulfide) (PAS) such as poly(phenylene sulfide) (PPS), an engineering plastic noted for its high strength and thermal stability. This sulfur source has some disadvantages, for example it is not readily soluble in the N-methylpyrrolidone solvent often used in the synthesis of PPS polymers and it is difficult to obtain an accurate analysis because of the variations in sulfur content between different batches of sodium hydrosulfide and changes that occur to this material upon storage. The proper ratio of sodium hydrosulfide/dichlorobenzene must be maintained in a very close range to obtain high quality PPS. N-Methylthiopyrrolidone is a potentially important alternative source of elemental sulfur for the poly(arylene sulfide) polymer synthesis because:

(1) it is more soluble in the usual polymer solvent medium which results in smoother process operations and less possibility of line plugging.

(2) it is a stable liquid that can be more accurately metered to obtain and maintain a high quality polymer.

(3) it is more economical because the source of elemental sulfur is calculated to be about $0.03/lb. of sulfur produced, 1/10 the cost of sulfur produced from sodium hydrosulfide.

It is known that N-methylthiopyrrolidone can be prepared from N-methylpyrrolidone and a variety of sulfur containing reagents, such as: elemental sulfur, carbonyl chloride/hydrogen sulfide, phosphorous pentasulfide, carbon disulfide, and hydrogen sulfide. All of these batch processes have certain disadvantages, the most common of which is inability or difficulty of operating the conversion as a continuous process. The process described below has been conducted in a continuous manner and is readily adaptable to large scale operation.

It is therefore an object of this invention to prepare thioamides from amides. In a more specific application it is an object of this invention to prepare thiolactams from lactams. It is yet another object of this invention to provide a process for the production of sulfur containing compounds using a continuous, mild temperature, catalyzed reaction.

Other aspects, objects, and the various advantages of this invention will become apparent upon reading this specification and the appended claims.

STATEMENT OF THE INVENTION

A method is provided for preparing thioamides from amides in which an amide is contacted with a source of sulfur in the presence of a sulfactive catalyst at an elevated temperature below 800° F. (427° C.). The reaction conditions described in this invention are considered mild and as such do not thermally promote the formation of a typical thioamide from an amide and a source of sulfur unless the reagents, which are premixed, are passed over a heated catalytic surface. The catalytic reaction produces the thioamide with high selectivity and in high yields thereby providing an improved process for the preparation of this material.

The amides which are employed in this invention are either cyclic or acyclic. Acyclic amides are represented by the formula:

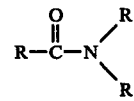

wherein each R is selected from the group consisting of hydrogen, alkyl and cycloalkyl radicals, and mixtures thereof. The hydrocarbon radicals can be saturated aliphatic, cycloaliphatic radicals and combinations thereof containing from 1 to 20 carbon atoms, inclusive.

The acyclic thioamides which are prepared by this invention are represented by the formula:

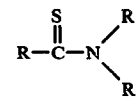

wherein R is as defined above.

Acyclic amides which can be converted to thioamides by this invention include formamide, N-methylformamide, N,N-dimethylformamide, N-ethylformamide, N,N-diethylformamide, acetamide, N-methylacetamide, N,N-dimethylacetamide, N-ethylacetamide, N,N-diethylacetamide, propionamide, N-methylpropionamide, N,N-dimethylpropionamide, N-ethylpropionamide, N,N-diethylpropionamide, and the like.

Cyclic amides, referred to as lactams, which are the preferred amides for use in this invention and are represented by the formula:

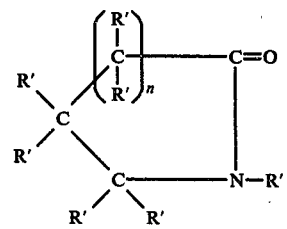

wherein each R' is selected from the group consisting of hydrogen, alkyl and cycloalkyl radicals, and mixtures thereof. The hydrocarbon radicals can be saturated aliphatic, cycloaliphatic radicals and combinations thereof containing from 1 to 6 carbon atoms, inclusive. n Can be an integer from 0 to 10, inclusive. The total number of carbon atoms in these lactams generally should not exceed 20.

The thiolactams which are prepared by this invention are represented by the formula:

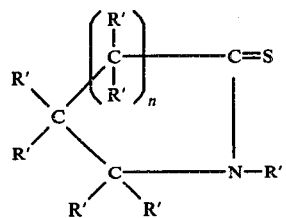

wherein R' and n are as defined above.

Lactams which can be converted to thiolactams by the process of this invention include 2-azetidinone, 2-pyrrolidinone, 2-piperidone, 2-oxohexamethylenimine(-caprolactam), 1-methyl-2-azetidinone, 1-methyl-2-pyrrolidinone, 2-oxo-1-ethylhexamethylenimine, 3,3-di-n-propyl-2-piperidone, 2-oxo-4-n-hexyl-hexamethylenimine, 2-oxo-1-cyclopentylhexamethylenimine, lactam of 7-(cyclohexylamino)-heptanoic acid, lactam of 13-aminotridecanoic acid, 3,4,5-tri-n-pentyl-2-piperidone, 3-cyclopentyl-2-pyrrolidinone, lactam of 8-amino-3-cyclohexyl-4-ethyloctanoic acid, 1-isopropyl-2-pyrrolidinone, 2-oxo-1-ethyl-3-tert-butylhexamethylenimine, and the like.

The source of sulfur in the present process is generally either hydrogen sulfide, carbon disulfide, carbonyl sulfide, or mixtures of these materials. Elemental sulfur can also be used but usually requires hydrogen as a co-reagent.

The catalysts which are employed in this invention are sulfactive type and generally acidic in nature. The preferred catalysts contain molybdenum or tungsten. Some examples of sulfactive catalysts are phosphotungstic acid, phosphomolybdic acid, molybdenum oxide, molybdenum sulfide, tungstic oxide, tungstic sulfide, molybdenum, molybdenum modified with other metals such as cobalt and nickel, tungsten, tungsten modified with other metals such as cobalt or nickel. These catalysts can be used without support but preferably are supported on such materials as alumina, silica, zeolite, and the like. The catalysts can be used individually or can be mixed with other catalysts and can be supported on a single support or a mixture of supports.

As stated above, the reaction conditions for the catalyzed preparation of thioamides described herein are considered to be mild, being carried out at an elevated temperature below 800° F. (427° C.). Within this limitation a broad range of reaction temperatures is about 300° to about 800° F. (149°–427° C.), with a preferred range of about 450° to about 650° F. (232°–343° C.). The reaction can be carried out at a pressure ranging from about 0 to about 1000 psia (0–6.89 MPa), with a preferred pressure rang of about 100 to about 500 psia (0.689–3.445 MPa).

Although the invention is operable over a broad range of molar ratios for the feed and with a broad range of feed rates, the usual range of molar ratio for the feed will be $H_2S$/amide of about 2.5/1 to about 10/1, with a preferred range of about 3.5/1 to about 5.0/1, and a molar ratio of feed of amide/$CS_2$ of about 1/1 to about 10/1, with a preferred range of about 1.6/1 to about 2.4/1. Similarly, the feed rate will usually fall withing a range of about 1.2 ml to about 7.8 ml per minute with a preferred range of about 2.0 to about 5.0 ml per minute for a system having hydrogen sulfide and amide components and will fall within a range of about 1.5 to about 5.0 ml per minute, with a preferred range of about 1.6 to about 2.4 ml per minute when the feed components are amide and carbon disulfide.

The following examples are offered to demonstrate the operability of this invention.

EXAMPLE I

The tubular reactor used was constructed of one-half inch I.D. schedule 40 pipe about 18 inches long and contained a thermocouple well of one-fourth inch tubing which extended the length of the reactor. Stainless steel was used in reactor construction as well as in all piping, valves, and gauges. The reactor was jacketed by three electrical heaters which were controlled by individual thermocouples on the outside wall of the pipe. All components of the feed were premixed at the desired ratio and were metered down-flow with a LS-30 Lapp pump. On the downstream side, pressure was controlled and products were removed by a Whitey 2RF2 valve operated by a Taylor Fulscope.

The tubular reactor was filled with a catalyst, about 2 wt. % phosphotungstic acid on alumina, and the tube and contents heated to about 600° F. (316° C.). The reactor was pressured to 1.172 MPa (170 psi) and a feed consisting of a 4/1 mole ratio of hydrogen sulfide/N-methylpyrrolidone (NMP) was fed into the reactor at a rate of about 1 ml NMP/min. After 7.75 hours, a total of about 482.1 g NMP had been fed into the reactor. The effluent was flashed distilled at 100° C./1.2 mm to remove excess hydrogen sulfide and analyzed by chromatography (GLC). These analysis indicated the following components:

|  | Overhead (463g) | | Residue (7g) | |
| --- | --- | --- | --- | --- |
|  | Wt. % | Grams | Wt. % | Grams |
| N-Methylpyrrolidone | 85.3 | 394.9 | 4.7 | 0.3 |
| Unknown | — | — | 0.7 | 0.05 |
| N-Methylthiopyrrolidone | 14.7 | 68.1 | 94.6 | 6.6 |

EXAMPLE II

The reaction described in Example I was repeated with the exception that the catalyst, phosphotungstic acid on alumina, was replaced with 80 ml of glass beads (3 mm diameter) and the reaction run for only 5.75 hours. The effluent was flashed distilled (42° C./0.2 mm) to remove the large excess of hydrogen sulfide and analyzed by GLC (265g). These analysis are shown as:

|  | Overhead (265g) | | Residue (4g) | |
| --- | --- | --- | --- | --- |
|  | Wt. % | Grams | Wt. % | Grams |
| N-Methylpyrrolidone | 98.93 | 262.2 | — | — |
| Unknown | 0.49 | 1.3 | — | — |
| N-Methylthiopyrrolidone | 0.58 | 1.5 | — | — |

EXAMPLE III

The tubular reactor was filled with a catalyst, about 2 wt. % phosphotungstic acid on alumina, and the tube and contents heated to about 600° F. (316° C.). The reactor was pressured to 3.44 MPa (500 psi) and a feed consisting of a 2.6/1 mole ratio of N-methylpyrrolidone/carbon disulfide was fed into the reactor at a rate of about 2 ml NMP and $CS_2$/min. After 5.5 hours, a total of 657.3 ml (447.8 ml or 459.4g N-methylpyrrolidone plus 209.5 ml or 264.5g carbon disulfide) was fed into the reactor. The effluent was flashed distilled at 98° C./1.2 mm. and analyzed by chromatography.

|  | Overhead (404g) |  | Residue (130g) |  |
|---|---|---|---|---|
|  | Wt. % | Grams | Wt. % | Grams |
| N-Methylpyrrolidone | 89.5 | 361.6 | 4.2 | 5.4 |
| Unknown | — | — | 0.2 | 0.3 |
| N-Methylthiopyrolidone | 10.5 | 42.4 | 95.6 | 124.3 |

EXAMPLE IV

The reaction described in Example III was repeated with the exception that the catalyst, phosphotungstic acid on alumina, was replaced with 80 ml of glass beads (3 mm diameter). The run was 5.5 hours long from which was collected 611g. The effluent was flashed distilled (95° C./0.7mm) to remove excess carbon disulfide and analyzed by GLC, the results of which are shown below.

|  | Overhead (300.2g) |  | Residue (140.2g) |  |
|---|---|---|---|---|
|  | Wt. % | Grams | Wt. % | Grams |
| N-Methylpyrrolidone | 100.0 | 300.2 | 99.7 | 139.8 |
| Unknown | — | — | 0.1 | 0.1 |
| N-Methylthiopyrrolidone | — | — | 0.2 | 0.3 |

Examples I through IV describe reactions involving the conversion of cyclic amides to cyclic thioamides. Based on these experiments the conversion of acyclic amides to acyclic thioamides are described in the following predictive runs, Examples V to VIII.

EXAMPLE V

The reaction described in Example III is repeated with the exception that the feed consists of a 2/1 mole ratio of N,N-dimethylacetamide (DMA)/carbon disulfide. After 4 hours, the collected product effluent is stripped of unreacted carbon disulfide to give about 349g of product residue. This residue is flashed distilled at about 100° C./80 mm and is analyzed by chromatography.

|  | Overhead (245g) |  | Residue (102g) |  |
|---|---|---|---|---|
|  | Wt. % | Grams | Wt. % | Grams |
| N,N-Dimethylacetamide (DMA) | 91 | 223 | 4 | 4 |
| Unknown | — | — | 5 | 5 |
| N,N-Dimethylthioacetamide | 9 | 22 | 91 | 92 |

EXAMPLE VI

The reaction described in Example V is repeated with the exception that the catalyst, phosphotungstic acid on alumina, is replaced with glass beads (3 mm diameter). The run is for 4 hours, after which excess carbon disulfide is removed by distillation to give about 334 of product which is further vacuum distilled at about 90°-100° C./80 mm and is analyzed by chromatography.

|  | Overhead (324g) |  | Residue (10g) |  |
|---|---|---|---|---|
|  | Wt. % | Grams | Wt. % | Grams |
| N,N-Dimethylactamide | 100 | 324 | 94 | 9 |
| Unknown | — | — | 5 | <1 |
| N,N-Dimethylthioactamide | — | — | 1 | <1 |

EXAMPLE VII

The reaction described in Example I is repeated with the exception that the feed consists of a 4/1 mole ratio of hydrogen sulfide/N,N-dimethylacetamide. After 4 hours the product is collected, excess hydrogen sulfide is weathered off leaving about 232g of product which is distilled at about 100° C./80 mm and is analyzed by chromatography.

|  | Overhead (175g) |  | Residue (55g) |  |
|---|---|---|---|---|
|  | Wt. % | Grams | Wt. % | Grams |
| N,N-Dimethylacetamide | 95 | 166 | 4 | 2 |
| Unknown | — | — | — | — |
| N,N-Dimethylthioacetamide | 5 | 9 | 96 | 53 |

EXAMPLE VIII

The reaction described in Example VII is again repeated with the exception that the catalyst, phosphotungstic acid on alumina, is replaced with glass beads (3mm diameter). The run is for 4 hours after which excess hydrogen sulfide is weathered off and the product vacuum distilled at about 90°-100° C./80mm and is analyzed by chromatography.

|  | Overhead (210g) |  | Residue (10g) |  |
|---|---|---|---|---|
|  | Wt. % | Grams | Wt. % | Grams |
| N,N-Dimethylacetamide | 100 | 210 | 98 | 10 |
| Unknown | — | — | 2 | <1 |
| N,N-Dimethylthioactamide | — | — | trace | — |

The following table summarizes the examples herein described.

| Ex. | Feed | Catalyst | Mole % Per Pass Yield | Mole % Utimate Ultimate Yield |
|---|---|---|---|---|
| I | H$_2$S/NMP | Phosphotungstic acid/alumina | 20.4 | 100.0 |
| II | " | None | <1.0 | <1.0 |
| III | CS$_2$/NMP | Phosphotungstic acid/alumina | 27.9 | 93.5 |
| IV | " | None | <1.0 | <1.0 |
| V | H$_2$S/DMA | Phosphotungstic acid/alumina | 29 | 97 |
| VI | " | None | <1.0 | <1.0 |
| VII | CS$_2$/DMA | Phosphotungstic acid/alumina | 21 | 89 |
| VIII | " | None | <1.0 | <1.0 |

It can readily be seen from the above data that using the same reaction conditions, a catalyst is necessary for the conversion of amides to thioamides at elevated temperatures below 800° F. (427° C.).

I claim:

1. A method for preparing thioamides from amides comprising contacting an amide chosen from acyclic compounds of the formula

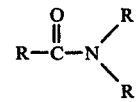

wherein each R is selected from the group consisting of hydrogen, alkyl and cycloalkyl radicals, and mixtures thereof and cyclic compounds of the formula

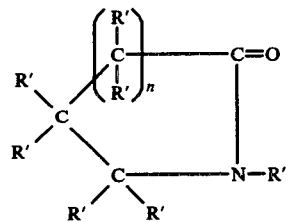

wherein each R' is selected from the group consisting of hydrogen, alkyl and cycloalkyl radicals and mixtures thereof and n is 0 to 10 with a source of sulfur in the presence of a sulfactive catalyst comprising molybdenum or tungsten at an elevated temperature in a range of about 300° to about 800° F. (149°–427° C.).

2. A method of claim 1 wherein said source of sulfur is chosen from elemental sulfur, $H_2S$, $CS_2$, COS, and mixtures thereof.

3. A method of claim 2 wherein the source of sulfur is elemental sulfur and hydrogen is present in the reaction mixture.

4. A method of claim 1 wherein the catalyst is chosen from phosphotungstic acid, phosphomolybdic acid, molybdenum oxide, molybdenum sulfide, tungstic oxide, tungstic sulfide, molybdenum, molybdenum modified with cobalt or nickel, tungsten, and tungsten modified with cobalt or nickel.

5. A method of claim 1 wherein the catalyst is supported.

6. A method of claim 2 wherein the amide is N-methylpyrrolidone and the source of sulfur is $H_2S$ or $CS_2$.

7. A method of claim 6 wherein the $H_2S$/NMP ratio is about 2.5/1 to about 10/1.

8. A method of claim 6 wherein the NMP/$CS_2$ ratio is about 1/1 to about 10/1.

9. A method of claim 7 wherein the catalyst is phosphotungstic acid on alumina.

10. A method of claim 8 wherein the catalyst is phosphotungstic acid on alumina.

* * * * *